(12) United States Patent
Moncada et al.

(10) Patent No.: US 10,961,210 B2
(45) Date of Patent: Mar. 30, 2021

(54) PRODUCTION OF SULFONYL AZIDE ANHYDRIDE

(71) Applicant: Dow Global Technologies LLC, Midland, MI (US)

(72) Inventors: Adriana I. Moncada, Midland, MI (US); Brian W. Walther, Clute, TX (US); Jerzy Klosin, Midland, MI (US); Ahmad E. Madkour, Canton, MI (US)

(73) Assignee: Dow Global Technologies LLC, Midland, MI (US)

( * ) Notice: Subject to any disclaimer, the term of this patent is extended or adjusted under 35 U.S.C. 154(b) by 149 days.

(21) Appl. No.: 16/310,979

(22) PCT Filed: Jun. 21, 2017

(86) PCT No.: PCT/US2017/038476
§ 371 (c)(1),
(2) Date: Dec. 18, 2018

(87) PCT Pub. No.: WO2017/223164
PCT Pub. Date: Dec. 28, 2017

(65) Prior Publication Data
US 2020/0308127 A1 Oct. 1, 2020

Related U.S. Application Data

(60) Provisional application No. 62/353,919, filed on Jun. 23, 2016.

(51) Int. Cl.
C07D 307/60 (2006.01)
C07D 307/93 (2006.01)

(52) U.S. Cl.
CPC ......... C07D 307/60 (2013.01); C07D 307/93 (2013.01)

(58) Field of Classification Search
CPC ........................... C07D 307/60; C07D 307/93
See application file for complete search history.

(56) References Cited

U.S. PATENT DOCUMENTS

| | | |
|---|---|---|
| 3,530,108 A | 9/1970 | Oppenlander |
| 3,616,199 A | 10/1971 | Breslow |
| 3,701,788 A | 10/1972 | Sayigh et al. |
| 4,031,068 A | 6/1977 | Cantor |
| 4,515,636 A | 5/1985 | Carney et al. |
| 4,666,631 A | 5/1987 | Udding |
| 4,861,843 A | 8/1989 | Udding et al. |
| 4,935,466 A | 6/1990 | Udding |
| 6,331,597 B1 | 12/2001 | Drumright et al. |
| 6,521,306 B1 | 2/2003 | Hoenig et al. |
| 6,552,129 B2 | 4/2003 | Babb et al. |
| 7,399,808 B2 | 7/2008 | Walters et al. |

FOREIGN PATENT DOCUMENTS

WO 2016/109628 A1 7/2016

*Primary Examiner* — Timothy R Rozof
(74) *Attorney, Agent, or Firm* — Quarles & Brady LLP

(57) ABSTRACT

The present disclosure provides a process for producing an aliphatic sulfonyl azide anhydride and the resultant aliphatic sulfonyl azide anhydride composition. The process includes: (i) thio-acetoxylating an alkenyl carboxylic acid anhydride to form a thioacetate anhydride intermediate, (ii) oxy chlorinating the thioacetate anhydride intermediate to form a sulfonyl chlorideanhydride intermediate; and (iii) azidizing the sulfonyl chloride anhydride intermediate to form an aliphatic sulfonyl azide anhydride.

15 Claims, No Drawings

PRODUCTION OF SULFONYL AZIDE ANHYDRIDE

BACKGROUND

The present disclosure relates to the production of sulfonyl azide anhydrides, and aliphatic sulfonyl azide anhydrides in particular, and a process for producing the same.

Known are aromatic sulfonyl azide anhydrides, such as 4-azidosulfonylphthalic anhydride. Such aromatic sulfonyl azide anhydrides are commonly grafted with an olefin-based polymer and used as a tie layer in multilayer films for food packaging and specialty packaging. The tie layer is typically used to bind a polyolefin layer to other layers containing a polar substrate, such as nylon, for example.

Desirable would be a non-aromatic bi-functional molecule having anhydride functionality and azo functionality, and a process for producing the same.

SUMMARY

The present disclosure provides a process for producing aliphatic sulfonyl azide anhydrides. The process includes: (i) thio-acetoxylating an alkenyl carboxylic acid anhydride to form a thioacetate anhydride intermediate, (ii) oxychlorinating the thioacetate anhydride intermediate to form a sulfonyl chloride anhydride intermediate; and (iii) azidizing the sulfonyl chloride anhydride intermediate to form an aliphatic sulfonyl azide anhydride.

The present disclosure also provides a composition containing an aliphatic sulfonyl azide anhydride. The aliphatic sulfonyl azide anhydride has a Structure (4):

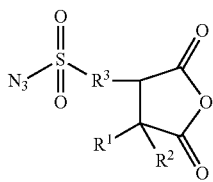

Structure (4)

wherein $R^1$, $R^2$, and $R^3$ may be the same or different; and $R^1$, $R^2$, and $R^3$ each is independently selected from a substituted $C_1$-$C_{40}$ hydrocarbonyl group, an unsubstituted $C_1$-$C_{40}$ hydrocarbonyl group, $Si(R^C)_3$, $OR^C$, $R^CC(O)O$—, $R^COC(O)$—, $R^CC(O)N(R)$—, $(R^C)_2NC(O)$—, a halogen atom, and a hydrogen atom, wherein $R^C$ is a $C_1$-$C_{30}$ hydrocarbonyl group;

with the proviso that at least one of $R^1$, $R^2$, and $R^3$ is selected from a substituted $C_1$-$C_{40}$ hydrocarbonyl group or an unsubstituted $C_1$-$C_{40}$ hydrocarbonyl group.

Definitions

Any reference to the Periodic Table of Elements is that as published by CRC Press, Inc., 1990-1991. Reference to a group of elements in this table is by the new notation for numbering groups.

For purposes of United States patent practice, the contents of any referenced patent, patent application or publication are incorporated by reference in their entirety (or its equivalent US version is so incorporated by reference) especially with respect to the disclosure of definitions (to the extent not inconsistent with any definitions specifically provided in this disclosure) and general knowledge in the art.

The numerical ranges disclosed herein include all values from, and including, the lower and upper value. For ranges containing explicit values (e.g., 1 or 2; or 3 to 5; or 6; or 7), any subrange between any two explicit values is included (e.g., 1 to 2; 2 to 6; 5 to 7; 3 to 7; 5 to 6; etc.).

Unless stated to the contrary, implicit from the context, or customary in the art, all parts and percents are based on weight and all test methods are current as of the filing date of this disclosure.

The term "composition" refers to a mixture of materials which comprise the composition, as well as reaction products and decomposition products formed from the materials of the composition.

The terms "comprising," "including," "having" and their derivatives, are not intended to exclude the presence of any additional component, step or procedure, whether or not the same is specifically disclosed. In order to avoid any doubt, all compositions claimed through use of the term "comprising" may include any additional additive, adjuvant, or compound, whether polymeric or otherwise, unless stated to the contrary. In contrast, the term "consisting essentially of" excludes from the scope of any succeeding recitation any other component, step, or procedure, excepting those that are not essential to operability. The term "consisting of" excludes any component, step, or procedure not specifically delineated or listed. The term "or," unless stated otherwise, refers to the listed members individually as well as in any combination. Use of the singular includes use of the plural and vice versa.

A "hydrocarbon" is a compound that contains only hydrogen and carbon atoms. The hydrocarbon can be (i) branched or unbranched, (ii) saturated or unsaturated (iii) cyclic or acyclic, and (iv) any combination of (i)-(iii). Nonlimiting examples of hydrocarbons include alkanes, alkenes, and alkynes.

A "hydrocarbonyl group" is a hydrocarbon having a valence (typically univalent). Nonlimiting examples of hydrocarbonyl groups include alkyl-, cycloalkyl-, alkenyl-, alkadienyl-, cycloalkenyl-, cycloalkadienyl-, and alkynyl- groups.

A "substituted hydrocarbonyl" and a "substituted hydrocarbon" is a hydrocarbonyl group that contains a heteroatom.

An "unsubstituted hydrocarbonyl" and an "unsubstituted hydrocarbon" is a hydrocarbonyl group that contains only hydrogen and carbon atoms. An unsubstituted hydrocarbonyl excludes heteroatoms.

A "heteroatom" refers to an atom other than carbon or hydrogen. The heteroatom can be a non-carbon atom from Groups IV, V, VI and VII of the Periodic Table. Nonlimiting examples of heteroatoms include: F, N, O, P, B, S, and Si.

The term "aliphatic" refers to a hydrocarbon in which the carbon atoms form a cyclic chain or an open chain that is straight or branched. An aliphatic compound may be (i) branched or unbranched, (ii) cyclic or acyclic, (iii) saturated or unsaturated, or (iv) a combination of (i)-(iii). An aliphatic compound excludes aromatic compounds.

An "aromatic compound" is a hydrocarbon with one or more rings that contain alternating single and double bonds in its chemical structure. An aromatic compound excludes aliphatic compounds.

DETAILED DESCRIPTION

The present disclosure provides a process for producing aliphatic sulfonyl azide anhydrides. The process includes: (i) thio-acetoxylating an alkenyl carboxylic acid anhydride to form a thioacetate anhydride intermediate, (ii) oxychlorinating the thioacetate anhydride intermediate to form a sulfonyl chloride anhydride intermediate; and (iii) azidizing the sulfonyl chloride anhydride intermediate to form an aliphatic sulfonyl azide anhydride.

The present disclosure also provides a composition containing an aliphatic sulfonyl azide anhydride having a Structure (4):

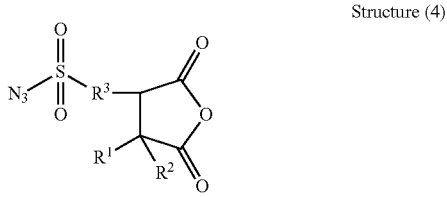

Structure (4)

wherein $R^1$, $R^2$, and $R^3$ may be the same or different; and $R^1$, $R^2$, and $R^3$ each is independently selected from a substituted $C_1$-$C_{40}$ hydrocarbonyl group, an unsubstituted $C_1$-$C_{40}$ hydrocarbonyl group, $Si(R^C)_3$, $OR^C$, $R^CC(O)O—$, $R^COC(O)—$, $R^CC(O)N(R)—$, $(R^C)_2NC(O)—$, a halogen atom, and a hydrogen atom, wherein $R^C$ is a $C_1$-$C_{30}$ hydrocarbonyl group;

with the proviso that at least one of $R^1$, $R^2$, and $R^3$ is selected from a substituted $C_1$-$C_{40}$ hydrocarbonyl group or an unsubstituted $C_1$-$C_{40}$ hydrocarbonyl group.

A. Process for Producing Aliphatic Sulfonyl Azide Anhydrides

The present disclosure provides a process for producing an aliphatic sulfonyl azide anhydride. The process includes: (i) thio-acetoxylating an alkenyl carboxylic acid anhydride to form a thioacetate anhydride intermediate, (ii) oxychlorinating the thioacetate anhydride intermediate to form a sulfonyl chloride anhydride intermediate; and (iii) azidizing the sulfonyl chloride anhydride intermediate to form an aliphatic sulfonyl azide anhydride.

1. Thio-acetoxylation

The present process includes the step of thio-acetoxylating an alkenyl carboxylic acid anhydride to form a thioacetate anhydride intermediate.

The "alkenyl carboxylic acid anhydride" has a $C_1$-$C_{40}$ alkenyl moiety with one or more double bonds and an anhydride moiety with two acyl groups bonded to the same oxygen atom.

In an embodiment, the alkenyl carboxylic acid anhydride has the following Structure (1):

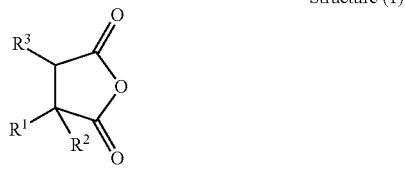

Structure (1)

wherein $R^1$, $R^2$, and $R^3$ may be the same or different; and $R^1$, $R^2$, and $R^3$ each is independently selected from a substituted $C_1$-$C_{40}$ hydrocarbonyl group, an unsubstituted $C_1$-$C_{40}$ hydrocarbonyl group, $Si(R^C)_3$, $OR^C$, $R^CC(O)O—$, $R^COC(O)—$, $R^CC(O)N(R)—$, $(R^C)_2NC(O)—$, a halogen atom, and a hydrogen atom, wherein $R^C$ is a $C_1$-$C_{30}$ hydrocarbonyl group;

with the proviso that at least one of $R^1$, $R^2$, and $R^3$ is selected from a substituted $C_1$-$C_{40}$ hydrocarbonyl group or an unsubstituted $C_1$-$C_{40}$ hydrocarbonyl group.

It is understood that at least one of $R^1$, $R^2$, and $R^3$ includes an alkenyl moiety with one or more double bonds.

The $R^1$, $R^2$, and $R^3$ groups may or may not combine to form a ring structure comprising from 3 to 5, or 8, or 12, or 20, or 40, or 50 carbon atoms. In an embodiment, at least two of the $R^1$, $R^2$, and $R^3$ groups in the alkenyl carboxylic acid anhydride of the Structure (1) combine to form a ring structure comprising from 3 to 50 carbon atoms. In another embodiment, the $R^1$ and $R^3$ groups in the alkenyl carboxylic acid anhydride of the Structure (1) form an unsubstituted $C_3$-$C_8$ hydrocarbonyl group ring structure.

In an embodiment, in the alkenyl carboxylic acid anhydride of the Structure (1), $R^1$ is an unsubstituted $C_1$-$C_{40}$, or $C_2$-$C_{40}$, or $C_1$-$C_{12}$, or $C_2$-$C_{12}$, or $C_1$-$C_8$ or $C_2$-$C_8$ hydrocarbonyl group; $R^2$ is hydrogen; $R^3$ is an unsubstituted $C_1$-$C_{40}$, or $C_2$-$C_{40}$, or $C_1$-$C_{12}$, or $C_2$-$C_{12}$, or $C_1$-$C_8$ or $C_2$-$C_8$ hydrocarbonyl group; and the $R^1$ and $R^3$ groups form a ring structure. A nonlimiting example of a suitable alkenyl carboxylic acid anhydride is endo-cis-bicyclo[2.2.1]hept-5-ene-2,3-dicarboxylic anhydride, commercially available from ACROS Organics. The structure of endo-cis-bicyclo[2.2.1]hept-5-ene-2,3-dicarboxylic anhydride is provided in Table 1 below as Structure (1a).

In an embodiment, in the alkenyl carboxylic acid anhydride of the Structure (1), $R^1$ and $R^2$ each is hydrogen and $R^3$ is an unsubstituted or $C_2$-$C_{40}$, or $C_1$-$C_{12}$, or $C_2$-$C_{12}$, or $C_1$-$C_8$ or $C_2$-$C_8$ hydrocarbonyl group. A nonlimiting example of a suitable alkenyl carboxylic acid anhydride is 2-methyl-2-propen-1-yl succinic anhydride, commercially available from TCI America. The structure of 2-methyl-2-propen-1-yl succinic anhydride is provided in Table 1 below as Structure (1b).

TABLE 1

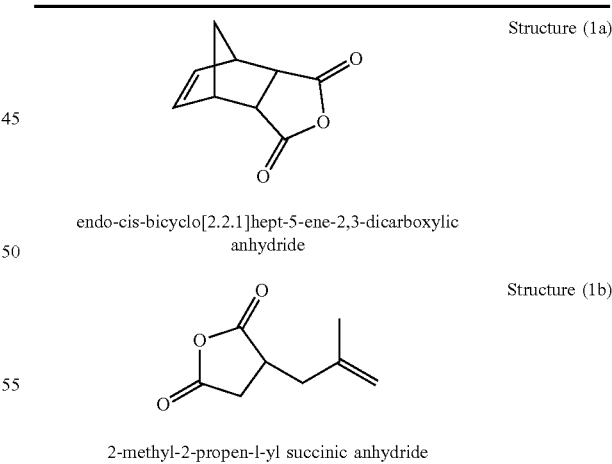

The alkenyl carboxylic acid anhydride may comprise two or more embodiments disclosed herein.

As used herein, "thio-acetoxylation" is a chemical reaction that bonds a thioacetyl functional group at the unsaturated hydrocarbon bond of the alkenyl carboxylic acid anhydride. In an embodiment, the thio-acetoxylation reaction is represented by the following Equation (1):

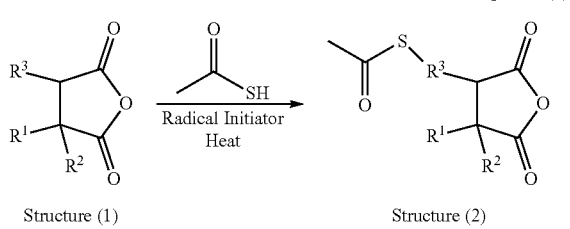

Equation (1)

Structure (1)     Structure (2)

wherein R³ of Structure (1) includes a hydrocarbonyl group with an alkenyl moiety.

It is understood that the R¹, R², and R³ groups of Structure (2) may or may not combine to form a ring structure comprising from 3 to 50 carbon atoms.

In Equation (1), Structure (1) represents the alkenyl carboxylic acid anhydride and Structure (2) represents the thioacetate anhydride intermediate.

Thioacetic acid has the following structure:

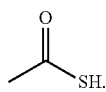

In an embodiment, the thio-acetoxylating includes reacting the alkenyl carboxylic acid anhydride with a thioacetic acid in the presence of a radical initiator to form a thioacetate anhydride intermediate. A "radical initiator" is a compound that is capable of catalyzing thio-acetoxylation of the alkenyl carboxylic acid anhydride with thioacetic acid to form a thioacetate anhydride intermediate. Nonlimiting examples of suitable radical initiators include azo-containing compounds and organic photoinitiators.

In an embodiment, the radical initiator is an azo-containing compound. In the presence of heat, the azo-containing radical initiator undergoes thermal decomposition to form free radicals, which react with the thiol group (—SH) of the thioacetic acid to form a thiyl radical species. The thiyl radical propagates with the alkenyl functional group via anti-Markovnikov addition to form a carbon-centered radical. Chain transfer abstracts a hydrogen from a thiol, which can then participate in multiple propagation steps. Nonlimiting examples of suitable azo-containing compounds include dimethyl 2,2'-azobis(2-methylpropionate), commercially available as V-601 from Wako Pure Chemical Industries, Ltd.; 2,2'-azobis(isobutyronitrile), commercially available as ARM from Wako Pure Chemical Industries, Ltd.; 2,2'-azobis(4-methoxy-2,4-dimethylvaleronitrile), commercially available as V-70 from Wako Pure Chemical Industries, Ltd.; 2,2-azobis(2,4-dimethylvaleronitrile), commercially available as V-65 from Wako Pure Chemical Industries, Ltd.; 2,2'-azobis(2-methylbutyronitrile), commercially available as V-59 from Wako Pure Chemical Industries, Ltd.; 1,1'-azobis(cyclohexane-1-carbonitrile), commercially available as V-40 from Wako Pure Chemical Industries, Ltd.; and 2,2'-azobis(N-butyl-2-methylpropionamide), commercially available as VAm-110 from Wako Pure Chemical Industries, Ltd.

In an embodiment, the radical initiator is an organic photoinitiator. In an embodiment, in the presence of ultraviolet (UV) light, the organic photoinitiator undergoes UV decomposition to form free radicals, which react with the thiol group (—SH) of the thioacetic acid to form a thiyl radical species. The thiyl radical propagates with the alkenyl functional group via anti-Markovnikov addition to form a carbon-centered radical. Chain transfer abstracts a hydrogen from a thiol, which can then participate in multiple propagation steps. Nonlimiting examples of suitable organic photoinitiators include benzophenone, commercially available from ACROS Organics; thioxanthone, commercially available from Sigma-Aldrich; camphorquinone, commercially available from Sigma-Aldrich; and 2,2-dimethoxy-2-phenyl acetophenone (DMPA), commercially available from Sigma-Aldrich.

In an embodiment, the thio-acetoxylating includes mixing endo-cis-bicyclo[2.2.1]hept-5-ene-2,3-dicarboxylic anhydride with thioacetic acid and dimethyl 2,2'-azobis(2-methylpropionate).

The azo-containing radical initiator may be dissolved in a solvent or may be added neat to the alkenyl carboxylic acid anhydride and/or the thioacetic acid. The solvent may be a hydrocarbon such as anhydrous toluene, for example. In an embodiment, the thio-acetoxylating includes (i) dissolving 2,2'-azobis(isobutyronitrile) in anhydrous toluene (from 0.1 Molar to 0.5 Molar) to form a radical initiator composition; and (ii) mixing endo-cis-bicyclo[2.2.1]hept-5-ene-2,3-dicarboxylic anhydride, the thioacetic acid, and the radical initiator composition at a temperature from 50° C., or 55° C., or 60° C., or 65° C. to 70° C., or 75° C., or 80° C., or 85° C., or 90° C. to form 5-(thioacetoxy)endo-cis-bicyclo[2.2.1]hept-5-ene-2,3-dicarboxylic anhydride as the thioacetate anhydride intermediate.

In an embodiment, the thio-acetoxylating includes reacting endo-cis-bicyclo[2.2.1]hept-5-ene-2,3-dicarboxylic anhydride with thioacetic acid in the presence of dimethyl 2,2'-azobis(2-methylpropionate) at a temperature from 50° C., or 55° C., or 60° C., or 65° C. to 70° C., or 75° C., or 80° C., or 85° C., or 90° C. to form 5-(thioacetoxy)endo-cis-bicyclo[2.2.1]hept-5-ene-2,3-dicarboxylic anhydride as the thioacetate anhydride intermediate.

In an embodiment, the thio-acetoxylating includes reacting 2-methyl-2-propen-1-yl succinic anhydride with thioacetic acid in the presence of dimethyl 2,2'-azobis(2-methylpropionate) at a temperature from 50° C., or 55° C., or 60° C., or 65° C. to 70° C., or 75° C., or 80° C., or 85° C., or 90° C. to form S-(3-(2,5-dioxotetrahydrofuran-3-yl)-2-methylpropyl) ethanethioate as the thioacetate anhydride intermediate.

The thio-acetoxylating may comprise two or more embodiments disclosed herein.

The thioacetate anhydride intermediate may or may not be purified prior to further processing.

2. Oxychlorination

The present process includes oxychlorinating the thioacetate anhydride intermediate to form a sulfonyl chloride anhydride intermediate.

As used herein, "oxychlorination" (also known as "oxidative chlorination") is a chemical reaction in which a thioester derivative is oxidized and chlorinated to the corresponding sulfonyl chloride. In an embodiment, the oxychlorination reaction is represented by the following Equation (2):

Equation (2)

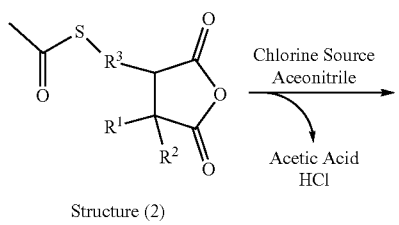

Structure (2)

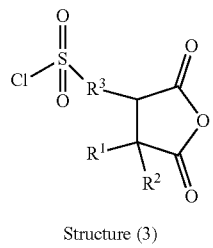

Structure (3)

It is understood that the $R^1$, $R^2$, and $R^3$ groups of Structure (3) may or may not combine to form a ring structure comprising from 3 to 50 carbon atoms.

In Equation (2), Structure (2) represents the thioacetate anhydride intermediate and Structure (3) represents the sulfonyl chloride anhydride intermediate.

Acetonitrile has the formula $CH_3CN$.

Nonlimiting examples of a suitable chlorine source include chlorine gas ($Cl_2$) in the presence of water (such as deionized water, for example); N-chlorosuccinimide ($C_4H_4ClNO_2$) in the presence of a hydrochloric acid aqueous solution (such as 12 N HCl, for example); thionyl chloride ($SOCl_2$) in the presence of hydrogen peroxide ($H_2O_2$); zirconium chloride ($ZrCl_4$) in the presence of hydrogen peroxide ($H_2O_2$); and chlorotrimethylsilane (($CH_3)_3SiCl$) in the presence of a nitrate salt. In an embodiment, the chlorine source is selected from chlorine gas, N-chlorosuccinimide, and combinations thereof.

The oxychlorination includes reacting the thioacetate anhydride intermediate and the chlorine source in a solvent (such as acetonitrile, for example) and optionally in the presence of water (such as deionized water, for example), hydrogen peroxide, a nitrate salt and/or a hydrochloric acid aqueous solution (such as 12 N HCl, for example).

In an embodiment, the oxychlorination includes reacting 5-(thioacetoxy)endo-cis-bicyclo[2.2.1]hept-5-ene-2,3-dicarboxylic anhydride with N-chlorosuccinimide in an acetonitrile/aqueous HCl solvent at a temperature from 0.1° C., or 0.8° C., or 1° C., or 5° C., or 8° C. to 10° C., or 15° C., or 20° C., or 22° C. to form 5-(chlorosulfonyl)endo-cis-bicyclo[2.2.1]heptane-2,3-dicarboxylic anhydride as the sulfonyl chloride anhydride intermediate.

In an embodiment, the oxychlorination includes reacting 5-(thioacetoxy)endo-cis-bicyclo[2.2.1]hept-5-ene-2,3-dicarboxylic anhydride and chlorine gas in an acetonitrile/water solvent at a temperature from 0.1° C., or 0.8° C., or 1° C., or 5° C., or 8° C. to 10° C., or 15° C., or 20° C., or 22° C. to form 5-(chlorosulfonyl)endo-cis-bicyclo[2.2.1]heptane-2,3-dicarboxylic anhydride as the sulfonyl chloride anhydride intermediate.

In an embodiment, the oxychlorination includes reacting S-(3-(2,5-dioxotetrahydrofuran-3-yl)-2-methylpropyl) ethanethioate and chlorine gas in an acetonitrile/water solvent at a temperature from 0.1° C., or 0.8° C., or 1° C., or 5° C., or 8° C. to 10° C., or 15° C., or 20° C., or 22° C. to form 3-(2,5-dioxotetrahydrofuran-3-yl)-2-methylpropane-1-sulfonyl chloride as the sulfonyl chloride anhydride intermediate.

The oxychlorinating may comprise two or more embodiments disclosed herein.

In an embodiment, the sulfonyl chloride anhydride intermediate is purified to remove the oxychlorination by-products of acetic acid ($CH_3COOH$) and hydrochloric acid prior to further processing.

3. Azidization

The present process includes azidizing the sulfonyl chloride anhydride intermediate to form an aliphatic sulfonyl azide anhydride.

As used herein, "azidization" or "azidizing" is a chemical reaction that replaces the chloro-group in the sulfonyl chloride anhydride intermediate with an azide group. In an embodiment, the azidization reaction is represented by the following Equation (3):

Equation (3)

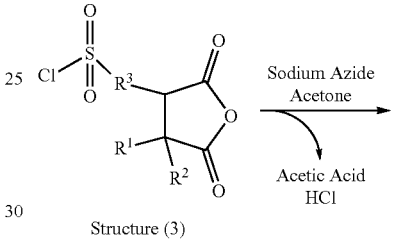

Structure (3)

Structure (4)

It is understood that the $R^1$, $R^2$, and $R^3$ groups of Structure (4) may or may not combine to form a ring structure comprising from 3 to 50 carbon atoms.

In Equation (3), Structure (3) represents the sulfonyl chloride anhydride intermediate and Structure (4) represents the aliphatic sulfonyl azide anhydride.

Sodium azide has the formula $N_3Na$.

Acetone has the formula $(CH_3)_2CO$.

In an embodiment, the azidizing includes reacting the sulfonyl chloride anhydride intermediate with sodium azide in the presence of a solvent, such as acetone, to form the aliphatic sulfonyl azide anhydride.

In an embodiment, the azidizing includes reacting 5-(chlorosulfonyl)endo-cis-bicyclo[2.2.1]heptane-2,3-dicarboxylic anhydride with sodium azide in the presence of acetone at a temperature from 20° C., or 21° C., or 22° C., or 23° C. to 24° C., or 25° C. to form 5-(azidosulfonyl)endo-cis-bicyclo[2.2.1]heptane-2,3-dicarboxylic anhydride as the aliphatic sulfonyl azide anhydride.

In an embodiment, the azidizing includes reacting 3-(2,5-dioxotetrahydrofuran-3-yl)-2-methylpropane-1-sulfonyl chloride with sodium azide in the presence of acetone at a temperature from 20° C., or 21° C., or 22° C., or 23° C. to 24° C., or 25° C. to form 3-(2,5-dioxotetrahydrofuran-3-yl)-2-methylpropane-1-sulfonyl azide as the aliphatic sulfonyl azide anhydride.

The azidization may comprise two or more embodiments disclosed herein.

In an embodiment, the aliphatic sulfonyl azide anhydride is purified to remove the azidization by-products such as sodium chloride (NaCl), for example.

The process may comprise two or more embodiments disclosed herein.

B. Composition Containing an Aliphatic Sulfonyl Azide Anhydride

The present disclosure provides a composition containing the aliphatic sulfonyl azide anhydride produced by the process disclosed herein. In an embodiment, the aliphatic sulfonyl azide anhydride is any aliphatic sulfonyl azide anhydride, and further any aliphatic sulfonyl azide anhydride of the Structure (4) disclosed herein.

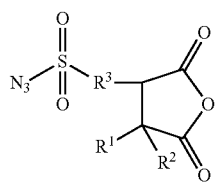

Structure (4)

wherein $R^1$, $R^2$, and $R^3$ may be the same or different; and $R^1$, $R^2$, and $R^3$ each is independently selected from a substituted $C_1$-$C_{40}$ hydrocarbonyl group, an unsubstituted $C_1$-$C_{40}$ hydrocarbonyl group, $Si(R^C)_3$, $OR^C$, $R^C C(O)O—$, $R^C OC(O)—$, $R^C C(O)N(R)—$, $(R^C)_2 NC(O)—$, a halogen atom, and a hydrogen atom, wherein $R^C$ is a $C_1$-$C_{30}$ hydrocarbonyl group;

with the proviso that at least one of $R^1$, $R^2$, and $R^3$ is selected from a substituted $C_1$-$C_{40}$ hydrocarbonyl group or an unsubstituted $C_1$-$C_{40}$ hydrocarbonyl group.

The $R^1$, $R^2$, and $R^3$ groups may or may not combine to form a ring structure comprising from 3, or 4 to 5, or 8, or 12, or 20, or 40, or 50 carbon atoms. In an embodiment, in the aliphatic sulfonyl azide anhydride of the Structure (4), at least two of the $R^1$, $R^2$, and $R^3$ groups combine to form a ring structure comprising from 3 to 50 carbon atoms. In another embodiment, in the aliphatic sulfonyl azide anhydride of the Structure (4), the $R^1$ and $R^3$ groups form an unsubstituted $C_3$-$C_8$, or $C_4$-$C_6$ hydrocarbonyl group ring structure.

In an embodiment, in the aliphatic sulfonyl azide anhydride of the Structure (4), the $R^1$, $R^2$, and $R^3$ groups are not combined into a ring structure.

The aliphatic sulfonyl azide anhydride is structurally distinct from a sulfonyl azide anhydride that contains an aromatic group because the aliphatic sulfonyl azide anhydride excludes aromatic compounds. Aliphatic compounds typically exhibit less absorbance in the UV range compared to aromatic compounds. Further, aliphatic sulfonyl azide anhydrides are more stable than aromatic sulfonyl azide anhydrides. More stable compounds are safer to use, and allow for the reactive moiety to be more uniformly dispersed during a functionalization step.

In an embodiment, the aliphatic sulfonyl azide anhydride of the Structure (4) includes one and only one azo functional group.

In an embodiment, in the aliphatic sulfonyl azide anhydride of the Structure (4), $R^2$ is hydrogen; and $R^1$ and $R^3$ form an unsubstituted $C_3$-$C_8$ hydrocarbonyl group ring structure. A nonlimiting example of a suitable aliphatic sulfonyl azide anhydride is 5-(azidosulfonyl)endo-cis-bicyclo[2.2.1]heptane-2,3-dicarboxylic anhydride, the structure of which is provided in Table 2 below as Structure (4a).

In an embodiment, in the aliphatic sulfonyl azide anhydride of the Structure (4), $R^1$ and $R^2$ each is hydrogen and $R^3$ is an unsubstituted $C_1$-$C_{12}$, or $C_1$-$C_8$ hydrocarbonyl group. A nonlimiting example of a suitable aliphatic sulfonyl azide anhydride is 3-(2,5-dioxotetrahydrofuran-3-yl)-2-methylpropane-1-sulfonyl azide, the structure of which is provided in Table 2 below as Structure (4b).

TABLE 2

Structure (4a)

5-(azidosulfonyl)endo-cis-bicyclo[2.2.1]heptane-2,3-dicarboxylic anhydride

Structure (4b)

3-(2,5-dioxotetrahydrofuran-3-yl)-2-methylpropane-1-sulfonyl azide

In an embodiment, the aliphatic sulfonyl azide anhydride is selected from 5-(azidosulfonyl)endo-cis-bicyclo[2.2.1]heptane-2,3-dicarboxylic anhydride, 3-(2,5-dioxotetrahydrofuran-3-yl)-2-methylpropane-1-sulfonyl azide, and combinations thereof.

In an embodiment, the aliphatic sulfonyl azide anhydride has a limiting impact energy as determined by the BAM Fall Hammer Test from 10 Joules (J), or 15 J, or 20 J, or 25 J, or 30 J, or 35 J, or 40 J, or 45 J, or 50 J, or 55 J, or 60 J to 70 J, or 75 J, or 80 J, or 90 J, or 100 J, or 150 J, or 200 J. The "limiting impact energy" refers to the minimum amount of mechanical impact energy applied to a sample that causes ignition. The present aliphatic sulfonyl azide anhydride is stable because it is less contact-explosive than traditional azides, which have a limiting impact energy of less than 10 J. A limiting impact energy of greater than or equal to 10 J, and further greater than or equal to 20 J, indicates the present aliphatic sulfonyl azide anhydride is safe for a user to handle.

The composition may comprise two or more embodiments disclosed herein.

Applications

Not wishing to be bound by any particular theory, the Applicants believe the aliphatic sulfonyl azide anhydride disclosed herein may be useful in the preparation of an aliphatic sulfonyl azide anhydride-grafted polyolefin tie layer for multilayer films, including multilayer films used in packaging applications such as food packaging and specialty packaging.

Test Methods

Density is measured in accordance with ASTM D792, Method B. The result is recorded in grams (g) per cubic centimeter (g/cc or g/cm$^3$).

Limiting impact energy is determined using the German Federal Institute for Testing Materials (BAM) Fall Hammer Test. Impact energy is imparted to a 40 mm$^3$ sample of the sulfonyl azide anhydride by a falling weight using the BAM Fall Hammer apparatus. The limiting impact energy is determined as the lowest energy at which a flash, flame or explosion is observed. The test assesses the sensitivity of the sulfonyl azide anhydride to drop-weight impact. The method yields quantitative results in the form of limiting impact energy. The testing is carried out at Chilworth Technology Inc., now part of DEKRA Insight. The limiting impact energy is measured in Joules (J).

$^1$H NMR

Samples are prepared by weighing 5 to 30 mg of the sample and dissolving it in a suitable deuterated nuclear magnetic resonance (NMR) solvent at room temperature (23° C.). The deuterated NMR solvents used are chloroform ($CDCl_3$), acetone (acetone-$d_6$) and dimethyl sulfoxide (DMSO-$d_6$), as shown in the experimental results detailed below. The NMR tubes utilized are from Norell (No. 502). The data are collected using a Varian 400 MR spectrometer or a VNMRS-500 spectrometer, both with pulse field gradient probes (PFB). The $^1$H NMR spectra is collected at a temperature of 25° C. or 30° C., as shown in the experimental results detailed below. The data are collected with 8 to 32 scans.

$^{13}$C NMR

The data are collected using a Varian UNITY Plus 400 MHz NMR spectrometer, corresponding to a $^{13}$C resonance frequency of 101 MHz, or a VNMR-500 spectrometer corresponding to a $^{13}$C resonance frequency of 126 MHz at a temperature of 25° C. or 30° C., as shown in the experimental results detailed below.

FTIR

Fourier transform infrared spectroscopy (FTIR) measurements are performed in transmission mode using a Perkin-Elmer Spectrum One spectrometer. The spectral range covered is 400-4500 cm$^{-1}$. For each measurement, 4 scans are taken and co-added with a spectral resolution of 4 cm$^{-1}$. Small amounts of neat samples are placed and analyzed in disposable PTFE (poly(tetrafluoroethylene)) infrared (IR) cards.

Mass Spectrometry

A. High Resolution Gas Chromatography Mass Spectrometry (HR GC/MS)

Samples are diluted into methylene chloride and 1 microliter aliquots of these solutions are analyzed by high resolution gas chromatography mass spectrometry (HR GC/MS) on an Agilent 7200 Accurate Mass Q-TOF GC/MS system, operating in the electron impact (IE) and positive ion chemical (PCI) ionization modes. Representative analysis conditions are provided in Table 3A below.

TABLE 3A

Column: 30 meter × 0.25 mm i.d. × 0.25 micron film Rtx-1, Restek Corp.
Temperatures:

Column: 60° C. for 2 minutes, heat to 300° C. at a rate of 10° C./min.
Injector: 280° C.                          Transfer Line: 320° C.
Source: 230° C. (EI) and 250° C. (PCI)     Quad: 150° C.
Flows:                                      Split: 80/1
Helium at 1.2 mL/minute (EI)
Ammonia (NH$_3$) at 20 mL/minute (PCI)
MS Detector: MCP: 650 V                    PMT: 811 V, +TOFMS,
CENT mode Fixed Emission: 35 μA (EI & PCI)
Electron Energy:
70 eV (EI)
100 eV (PCI)

TABLE 3A-continued

Scan:
35 to 800 amu (EI)
65 to 900 amu (PCI)
Rate: 10 scans/second per mode 2 GHz
EDR
Transients per spectrum: 1338
Solvent Delay: 2.5 minutes          N$_2$ Collision Gas: 1.5 mL/min
GC-QTOF auto-mass calibrated between EI analyses with
perfluorotributylamine (PFTBA) and at the start of the PCI analyses.

B. Atmospheric Pressure Chemical Ionization Mass Spectrometry (APCI)

Samples are dissolved in methylene chloride and 1 to 4 microliter aliquots of these solutions are analyzed by flow injection analysis (FIA) using accurate mass atmospheric pressure chemical ionization/mass spectrometry/mass spectrometry (APO/MS/MS) operating in the positive and negative (PI/NI) ion modes on an Agilent Model G1312B gradient liquid chromatography system coupled to an Agilent G6520B Q-TOF quadrupole/time of flight MS/MS system. No chromatographic separation takes place in flow injection analysis. The sample solution is injected into a flowing eluent stream directly into the ion source of the mass spectrometer. Representative analysis conditions are provided in Table 3B below.

TABLE 3B

Mobile Phase: A = methanol with 15 mM ammonium formate
Total Run Time: 4 minutes
Solvent Flow: 0.4 mL/min.
UV detection: 210 to 600 nm
APCI Conditions:
Gas temperature: 200° C.
Vaporizer temperature: 250° C.
Gas Flow: 8 L/min.
Capillary: 3.5 kV
Nebulizer: 45 PSI
Fragmentor: 155 V
Corona: 4 V (+)
Resolution:
10000 (+/−) 2 GHz Extended Dynamic Range
Mode: Centroid only
MS Scan Range:
90 to 1700 amu (+MS)
75 to 1700 amu (−MS)
Scan Rate: 1.3 scans/second
Reference Ions:
922.009798 (+)
966.000725 (−)

Aliquots of sample solutions are also analyzed by APO/MS/MS operating in the PI mode. Analysis conditions are the same as provided in Table 3B, except that the MS scan range is 100 to 1000 amu (+) with a MS scan rate of 5 scans/second; the MS/MS scan range is 20 to 1000 amu (+) with a MS/MS scan rate of 3 scans/second; the isolation width is 4 amu (medium); the fixed collision energy is 30V; the maximum precursors per cycle is 2; the threshold is 5000 counts; and the collision gas is N$_2$ at 30 psig.

By way of example, and not limitation, some embodiments of the present disclosure will now be described in detail in the following Examples.

EXAMPLES

Materials used in examples are provided in Table 4 below.

TABLE 4

| Material | Properties | Source |
| --- | --- | --- |
| Endo-cis-bicyclo[2.2.1]hept-5-ene-2,3-dicarboxylic anhydride | Powder solid at room temperature (23° C.) Density = 1.080 g/cc; CAS Number 129-64-6 | ACROS Organics |
| 2-methyl-2-propen-1-yl succinic anhydride | Crystal powder solid at room temperature (23° C.) CAS Number 18908-20-8 | TCI America |
| Thioacetic acid | Liquid at room temperature (23° C.) CAS Number 507-09-5 | Sigma-Aldrich |
| V-601 | Radical Initiator; CAS Number 2589-57-3 dimethyl 2,2'-azobis(2-methylpropionate) | Wako Pure Chemical Industries, Ltd. |
| AIBN | Radical Initiator; CAS Number 78-67-1 2,2'-azobis(isobutyronitrile) | Wako Pure Chemical Industries, Ltd. |
| N-chlorosuccinimide | $C_4H_4ClNO_2$; CAS Number 128-09-6 Solid at room temperature (23° C.) | Sigma-Aldrich |
| Chlorine gas | $Cl_2$ | |
| 12N HCl | Hydrochloric acid aqueous solution | |
| Acetonitrile | $CH_3CN$; CAS Number 75-05-8 | Fischer Scientific |
| Acetone | $(CH_3)_2CO$; CAS Number 67-64-1 | |
| Sodium azide | $N_3Na$; CAS Number 26628-22-8 Density = 1.850 g/cc Solid at room temperature (23° C.) | Sigma-Aldrich |

A. Production of 5-(azidosulfonyl)endo-cis-bicyclo[2.2.1]heptane-2,3-dicarboxylic anhydride 1. Thio-acetoxylation of endo-cis-bicyclo[2.2.1]hept-5-ene-2,3-dicarboxylic anhydride The thio-acetoxylation of endo-cis-bicyclo[2.2.1]hept-5-ene-2,3-dicarboxylic anhydride is depicted in Equation (1a):

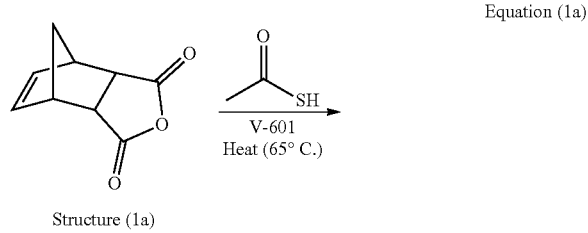

Equation (1a)

Structure (1a)

In a 250 milliliter (mL) 2-neck round bottomed flask fitted with a condenser and a rubber septum are placed (i) 20 grams (0.122 mol) of endo-cis-bicyclo[2.2.1]hept-5-ene-2,3-dicarboxylic anhydride (Structure (1a)), (ii) 37.1 grams (35 mL, 0.49 mol) thioacetic acid, and (iii) 0.5 grams V-601 initiator. The components are mixed and the mixture is purged with $N_2$ for 5 minutes. The flask is then placed in an oil bath set at 65° C. The mixture is heated to 65° C. for 5 hours. The flask is then removed from the oil bath and the mixture is cooled to room temperature (23° C.). After cooling, 5-(thioacetoxy)endo-cis-bicyclo[2.2.1]hept-5-ene-2,3-dicarboxylic anhydride is purified by including hexane in the mixture and stirring the mixture, which forms 28 grams of a white precipitate. The white precipitate is washed with hexane and dried under a vacuum. The product formed is 5-(thioacetoxy)endo-cis-bicyclo[2.2.1]hept-5-ene-2,3-dicarboxylic anhydride, depicted as Structure (2a) in Equation (1a) above. The reaction achieves a 96% yield of 5-(thioacetoxy)endo-cis-bicyclo[2.2.1]hept-5-ene-2,3-dicarboxylic anhydride.

$^1$H NMR (400 MHz, CDCl$_3$, 30° C.): δ 3.54 (dd, J=10.2, 5.4 Hz, 1H), 3.47 (dd, J=5.3, 1.9 Hz, 1H), 3.45-3.40 (m, 1H), 2.88-2.80 (m, 1H), 2.76-2.68 (m, 1H), 2.24 (s, 3H), 2.00 (ddd, J=15.0, 8.6, 2.5 Hz, 1H), 1.80 (dt, J=10.8, 1.5 Hz, 1H), 1.73-1.64 (m, 1H), 1.58 (dtd J=14.9, 4.7, 1.9 Hz, 1H).

$^{13}$C NMR (101 MHz, CDCl$_3$, 30° C.): δ 194.70, 171.75, 170.94, 49.56, 48.98, 46.55, 40.63, 40.44, 40.10, 33.49, 30.27.

2. Oxychlorination of 5-(thioacetoxy)endo-cis-bicyclo[2.2.1]hept-5-ene-2,3-dicarboxylic anhydride i. Oxychlorination with N-Chlorosuccinimide The oxychlorination of 5-(thioacetoxy)endo-cis-bicyclo[2.2.1]hept-5-ene-2,3-dicarboxylic anhydride with N-chlorosuccinimide is depicted in Equation (2a):

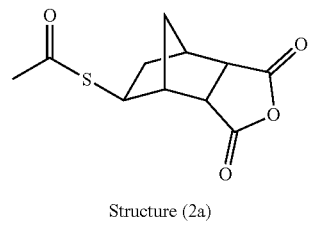

Structure (2a)

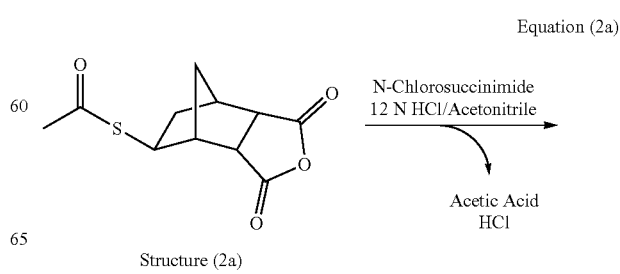

Equation (2a)

Structure (2a)

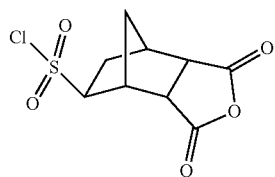

Structure (3a)

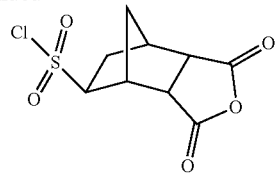

Structure (3a)

In a 250 mL Erlenmeyer flask cooled to 10° C. in an ice/water bath are placed (i) 22.2 grams N-chlorosuccinimide (167 mmol) and (ii) a mixture of 65 mL acetonitrile and 2 mL 12 N HCl. The components are mixed and left to stir for 10 minutes. Then, 10 grams of 5-(thioacetoxy)endo-cis-bicyclo[2.2.1]hept-5-ene-2,3-dicarboxylic anhydride (Structure (2a)) are included in the mixture as a solid in small portions, during which time the reaction temperature increases to 15° C. After the inclusion of the 5-(thioacetoxy)endo-cis-bicyclo[2.2.1]hept-5-ene-2,3-dicarboxylic anhydride is complete, the mixture is stirred at 20° C. for 20 minutes. Then, 400 mL ethyl acetate is included in the mixture and an organic layer forms. The organic layer is separated, washed with water (4 washes with 400 mL water per wash), and washed with saturated aqueous sodium chloride solution. The washed organic layer is then dried with anhydrous sodium sulfate. The dried organic layer is filtered using a disposable filter funnel and the solvent is evaporated under a vacuum to produce 11.07 grams of solid product. The solid product is stirred with 70 mL dichloromethane under $N_2$ overnight, filtered using a disposable filter funnel, and dried under a vacuum to yield 8.1 grams of 5-(chlorosulfonyl)endo-cis-bicyclo[2.2.1]heptane-2,3-dicarboxylic anhydride, depicted as Structure (3a) in Equation (2a) above. The reaction achieves a 73.7% yield of 5-(chlorosulfonyl)endo-cis-bicyclo[2.2.1]heptane-2,3-dicarboxylic anhydride.

$^1$H NMR (400 MHz, acetone-$d_6$, 30° C.): δ 4.04 (ddd, J=8.7, 5.7, 1.6 Hz, 1H), 3.98 (dd, J=10.3, 5.7 Hz, 1H), 3.82 (ddd, J=10.3, 5.4, 1.9 Hz, 1H), 3.53-3.44 (m, 1H), 3.15-3.06 (m, 1H), 2.44-2.34 (m, 1H), 2.24-2.14 (m, 2H), 1.96 (ddq, J=11.0, 3.0, 1.5 Hz, 1H).

$^{13}$C NMR (101 MHz, acetone-$d_6$, 30° C.): δ 171.99, 171.63, 74.65, 50.47, 49.70, 44.18, 40.72, 40.51, 31.04.

ii. Oxychlorination with Chlorine Gas

The oxychlorination of 5-(thioacetoxy)endo-cis-bicyclo[2.2.1]hept-5-ene-2,3-dicarboxylic anhydride with chlorine gas is depicted in Equation (2a'):

In a 250 mL 3-neck round bottomed flask are placed (i) 5.0089 grams (20.84 mmol) of 5-(thioacetoxy)endo-cis-bicyclo[2.2.1]hept-5-ene-2,3-dicarboxylic anhydride (Structure (2a)), (ii) 150 mL acetonitrile, and (iii) 5 mL water. The flask is fitted with a thermometer, a polyethylene tube as a gas inlet, and a gas outlet connected to a gas scrubber filled with a 25% sodium hydroxide aqueous solution. The flask is placed in an ice/water bath and the components are mixed using a magnetic stir bar. The temperature of the mixture reaches 0.8° C. The mixture is then purged with $N_2$ for 5 minutes. Subsequently, chlorine gas is bubbled slowly through the mixture while the temperature of the mixture increases to 13.8° C. over 17 minutes. When the chlorine gas is first introduced, the mixture is colorless due to the consumption of chlorine. The chlorine gas feed is stopped when the temperature of the mixture reaches 8.2° C., at which point the color of the mixture is a bright yellow. After the chlorine gas feed is stopped, the flask is removed from the ice/water bath and the mixture is purged with $N_2$ for 45 minutes, during which time the mixture becomes colorless. The mixture is partially concentrated down using a rotary evaporator. Water is subsequently included in the mixture until a white precipitate forms. The white precipitate is filtered off using a fritted glass funnel, washed with water, and dried under a vacuum to yield 3.94 grams of 5-(chlorosulfonyl)endo-cis-bicyclo[2.2.1]heptane-2,3-dicarboxylic anhydride, depicted as Structure (3a) in Equation (2a') above. The reaction achieves a 71.5% yield of 5-(chlorosulfonyl)endo-cis-bicyclo[2.2.1]heptane-2,3-dicarboxylic anhydride.

$^1$H NMR (400 MHz, acetone-$d_6$, 30° C.): δ 4.03 (ddd, J=8.7, 5.7, 1.6 Hz, 1H), 3.98 (dd, J=10.3, 5.7 Hz, 1H), 3.82 (ddd, J=10.3, 5.4, 1.8 Hz, 1H), 3.54-3.45 (m, 1H), 3.15-3.07 (m, 1H), 2.46-2.33 (m, 1H), 2.23-2.15 (m, 2H), 1.96 (ddq, J=11.0, 2.9, 1.5 Hz, 1H).

$^{13}$C NMR (101 MHz, acetone-$d_6$, 30° C.): δ 171.96, 171.63, 74.81, 50.54, 49.78, 44.29, 40.78, 40.59, 31.12.

3. Azidization of 5-(chlorosulfonyl)endo-cis-bicyclo[2.2.1]heptane-2,3-dicarboxylic anhydride The azidization of 5-(chlorosulfonyl)endo-cis-bicyclo[2.2.1]heptane-2,3-dicarboxylic anhydride is depicted in Equation (3a):

Equation (2a')

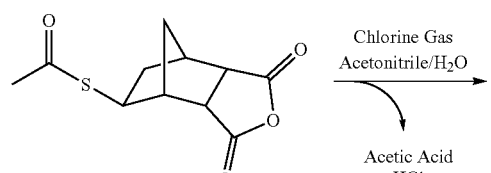

Structure (2a)

Equation (3a)

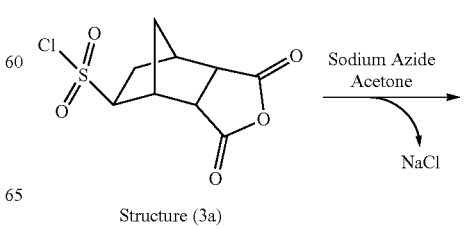

Structure (3a)

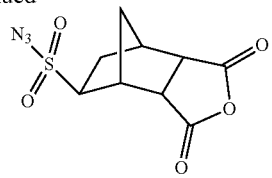

Structure (4a)

In a 20 mL vial, 1.0 gram (3.78 mmol) of the 5-(chlorosulfonyl)endo-cis-bicyclo[2.2.1]heptane-2,3-dicarboxylic anhydride produced using N-chlorosuccinimide is dissolved in 7 mL acetone. Then, 0.27 grams (4.15 mmol) sodium azide is included in the vial. The components are mixed and stirred overnight at room temperature (23° C.). The mixture is filtered using a disposable filter funnel and solvent is evaporated under a vacuum using a rotary evaporator to produce a white solid. The white solid is dissolved in ethyl acetate, washed with water, dried over anhydrous sodium sulfate, and filtered using a disposable filter funnel. Solvent is evaporated from the filtrate using a rotary evaporator and the product is mixed with a dichloromethane/hexane solution. 5-(azidosulfonyl)endo-cis-bicyclo[2.2.1]heptane-2,3-dicarboxylic anhydride is crystallized from the dichloromethane/hexane solution to yield 0.66 grams 5-(azidosulfonyl)endo-cis-bicyclo[2.2.1]heptane-2,3-dicarboxylic anhydride, depicted as Structure (4a) in Equation (3a) above. The reaction achieves a 65% yield of 5-(azidosulfonyl)endo-cis-bicyclo[2.2.1]heptane-2,3-dicarboxylic anhydride.

$^1$H NMR (400 MHz, DMSO-d$_6$, 30° C.): trace dichloromethane in sample, δ 3.84 (ddd, J=8.7, 5.7, 1.4 Hz, 1H), 3.74 (dd, J=10.2, 5.6 Hz, 1H), 3.62 (ddd, J=10.2, 5.4, 1.8 Hz, 1H), 3.24-3.13 (m, 1H), 2.94-2.82 (m, 1H), 2.09-2.0 (m, 1H), 1.98 (dt, J=10.6, 1.6 Hz, 1H), 1.90 (ddd, J=14.7, 8.7, 2.6 Hz, 1H), 1.72 (ddq, J=10.6, 2.9, 1.5 Hz, 1H).

$^{13}$C NMR (101 MHz, DMSO-d$_6$, 30° C.): δ 171.98, 171.35, 62.98, 49.50, 48.74, 41.96, 39.89, 38.81, 29.11.

The 5-(azidosulfonyl)endo-cis-bicyclo[2.2.1]heptane-2,3-dicarboxylic anhydride has a limiting impact energy of greater than 60 Joules, measured in accordance with the BAM Fall Hammer Test.

The crystal data and structure refinement for 5-(azidosulfonyl)endo-cis-bicyclo[2.2.1]heptane-2,3-dicarboxylic anhydride with Structure (4a) is provided in Table 5 below.

B. Production of 3-(2,5-dioxotetrahydrofuran-3-yl)-2-methylpropane-1-sulfonyl azide

1. Thio-acetoxylation of 2-methyl-2-propen-1-yl succinic anhydride

The thio-acetoxylation of 2-methyl-2-propen-1-yl succinic anhydride is depicted in Equation (1b):

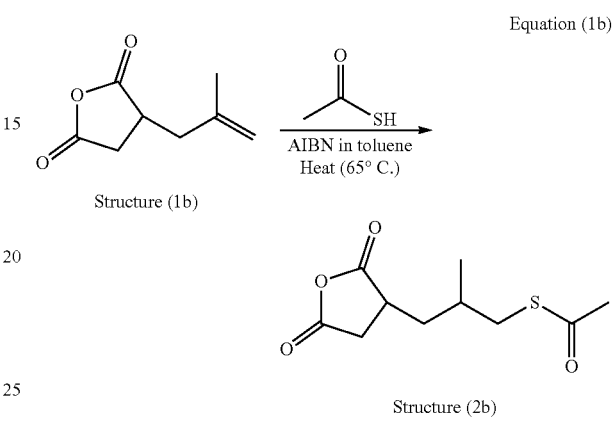

Equation (1b)

In a 500 mL Schlenk flask equipped with a magnetic stir bar and a septum is placed 12.04 grams (0.0780 mol) 2-methyl-2-propen-1-yl succinic anhydride. A solution containing AIBN initiator dissolved in anhydrous toluene (31 mL of a 0.2 M solution, equivalent to 1.018 grams (0.0062 moles) of AIBN) is transferred via syringe to the Schlenk flask containing the 2-methyl-2-propen-1-yl succinic anhydride. Then, 23 mL (0.3217 mol) thioacetic acid is transferred to the flask via syringe. The flask is connected to a scrubber containing bleach, and the outlet of the scrubber is connected to a bubbler. The components are mixed and the mixture is purged with N$_2$ for 10 minutes. Then, the mixture is heated to 65° C. using a heating block and stirred at 65° C. under nitrogen for 24 hours. Then, the majority of the unreacted thioacetic acid and toluene is evaporated using a rotary evaporator. Purification of the S-(3-(2,5-dioxotetrahydrofuran-3-yl)-2-methylpropyl) ethanethioate is achieved by column chromatography (utilizing an Teledyne ISCO™ instrument, eluting with hexanes:ethyl acetate in the follow-

TABLE 5

Crystal data and structure refinement for 5-(azidosulfonyl)endo-cis-bicyclo[2.2.1]heptane-2,3-dicarboxylic anhydride.

| | |
|---|---|
| Empirical formula: C$_9$H$_9$N$_3$O$_5$S | Formula weight: 271.25 |
| Temperature: 100(2) K | Wavelength: 0.71073 Å |
| Crystal system: Orthorhombic | Space group: Pca2(1) |
| Unit cell dimensions: | Volume: 2172.99(10) Å$^3$ |
| a = 15.8533(4) Å   α = 90° | |
| b = 6.6596(2) Å    β = 90° | |
| c = 20.5821(5) Å   γ = 90° | |
| Z: 8 | Density (calculated): 1.658 mg/m$^3$ |
| Absorption coefficient: 0.318 mm$^{-1}$ | F(000): 1120 |
| Crystal size: 0.56 × 0.28 × 0.10 mm$^3$ | Theta range for data collection: 1.98 to 27.50° |
| Index ranges: −13 <= h <= 20, −8 <= k <= 6, −20 <= l <= 26 | Reflections collected: 10572 |
| Independent reflections: 4589 [R(int) = 0.0173] | Completeness to theta = 27.50°: 100.0% |
| Absorption correction: Semi-empirical | Max. and min. transmission: 0.9689 and 0.8422 |
| Refinement method: Full-matrix least-squares on F$^2$ | Data/restraints/parameters: 4589/1/325 |
| Goodness-of-fit on F$^2$: 1.237 | Absolute structure parameter: 0.49(5) |
| Final R indices [I > 2sigma(I)]: R1 = 0.0312, wR2 =0.0845 | R indices (all data): R1 = 0.0333, wR2 = 0.0863 |
| Largest diff. peak and hole: 0.833 and −0.364 e ·Å$^{-3}$ | | ing ratios: 90:10, 85:15, 80:20, 60:40, and 0:100 (volume: volume)). The product is collected from fraction numbers 36-43 with a hexanes:ethyl acetate ratio of 80:20. The remaining solvent is removed in a rotary evaporator yielding 10.6 grams of a light yellow oily material, the S-(3-(2,5-dioxotetrahydrofuran-3-yl)-2-methylpropyl) ethanethioate, depicted as Structure (2b) in Equation (1b) above. The reaction achieves a 59.15% yield of S-(3-(2,5-dioxotetrahydrofuran-3-yl)-2-methylpropyl) ethanethioate.

$^1$H NMR (500 MHz, CDCl$_3$, 25° C., mixture of isomers in 1:1 ratio): trace ethyl acetate in sample, δ 3.31-3.13 (m, 3H), 3.07 (ddd, J=18.5, 9.8, 0.5 Hz, 1H), 2.94 (dd, J=13.7, 4.8 Hz, 1H), 2.88-2.77 (m, 2H), 2.68-2.57 (2 m overlapping, 3H), 2.30 (m, 6H), 1.97 (ddd, J=13.8, 7.9, 5.7 Hz, 1H), 1.86-1.71 (m, 3H), 1.69-1.61 (m, 1H), 1.48 (ddd, J=14.0, 9.3, 6.4 Hz, 1H), 0.98 (d, J=6.7 Hz, 3H), 0.96 (d, J=6.3 Hz, 3H).

$^{13}$C NMR (126 MHz, CDCl$_3$, 25° C., mixture of isomers in 1:1 ratio): δ 195.67, 195.55, 173.94, 173.81, 170.10, 170.03, 38.64, 37.01, 36.68, 35.36, 34.67, 34.51, 34.35, 31.71, 31.59, 30.61, 19.58, 18.43.

HR GC/MS/EI (PCI—NH$_3$) (M+NH$_4$)$^+$: m/z calculated for C$_{10}$H$_{18}$NO$_4$S$^+$: 248.0956, found: 248.09466 and 248.08587.

FTIR (cm$^{-1}$): 1860 (C=O), 1780 (C=O), 1688 (S=O).

2. Oxychlorination of S-(3-(2,5-dioxotetrahydrofuran-3-yl)-2-methylpropyl) ethanethioate The oxychlorination of S-(3-(2,5-dioxotetrahydrofuran-3-yl)-2-methylpropyl) ethanethioate with chlorine gas is depicted in Equation (2b):

Equation (2b)

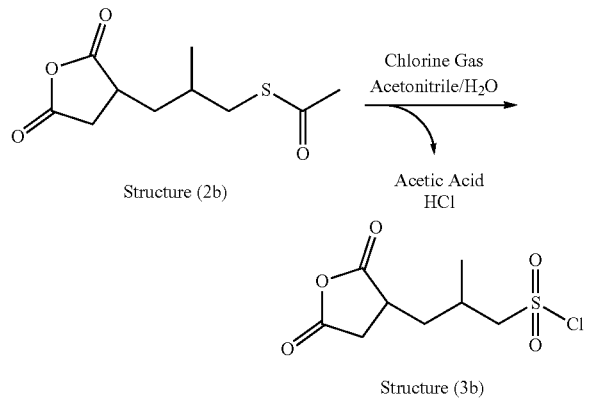

In a 500 mL 3-neck round bottomed flask are placed (i) 9.32 grams (0.0404 mol) of S-(3-(2,5-dioxotetrahydrofuran-3-yl)-2-methylpropyl) ethanethioate (Structure (2b)), (ii) 260 mL acetonitrile, and (iii) 3.15 mL deionized water. The flask is fitted with a thermometer, a polyethylene tube as a gas inlet, and a gas outlet connected to a gas scrubber filled with a 25% sodium hydroxide aqueous solution. The flask is placed in an ice/water bath and the components are mixed using a magnetic stir bar. The mixture is cooled to 3° C. The mixture is purged with N$_2$ for 5 minutes. Subsequently, chlorine gas is bubbled slowly through the mixture. When the chlorine gas is first introduced, the mixture is colorless. The temperature of the mixture rises to 14° C. after 20 minutes and 33 seconds of exposure to chlorine gas. The chlorine gas feed is stopped when the mixture becomes a green-yellow color. The chlorine gas feed is stopped after 50 minutes, at which point the temperature of the reaction is 6° C. After the chlorine gas feed is stopped, the 25% sodium hydroxide aqueous solution in the scrubber is replaced with fresh 25% sodium hydroxide aqueous solution. The flask is removed from the ice/water bath and the mixture is purged with N$_2$ for 2 hours and 10 minutes, after which the mixture becomes clear. The mixture is then concentrated in a rotary evaporator, dissolved in 200 mL of dichloromethane, and washed with deionized water (twice with 40 mL water, twice with 60 mL water, and twice with 80 mL water). During the washing with deionized water, an emulsion is formed. White precipitate is visible in the aqueous layer of the emulsion. To aid in breaking up the emulsion, 20 mL dichloromethane is included, forming an organic layer. The organic layer is separated, dried with magnesium sulfate, and filtered using a fritted glass funnel. Remaining solvent is evaporated from the filtrate using a rotary evaporator. The collected material is analyzed by $^1$H NMR and found to include 3-(2,5-dioxotetrahydrofuran-3-yl)-2-methylpropane-1-sulfonyl chloride.

$^1$H NMR (500 MHz, CDCl$_3$, 25° C.): δ 3.78-3.70 (m, 3H), 3.68 (dd, J=14.3, 6.3 Hz, 1H), 3.30-3.10 (m, 4H), 2.75-2.69 (m, 2H), 2.69-2.62 (m, 1H), 2.51-2.38 (m, 1H), 2.30-2.20 (m, 1H), 2.07-1.96 (m, 3H), 1.77-1.65 (m, 1H), 1.30 (d, J=6.8 Hz, 3H), 1.26 (d, J=6.8 Hz, 3H).

The collected material is then dissolved in 200 mL ethyl acetate and washed with water four times (60 mL water per wash). An organic layer forms. The organic layer is separated and 20 mL ethyl acetate is included. The organic layer/ethyl acetate solution is dried with magnesium sulfate and filtered using a fritted glass funnel. The remaining solvent is evaporated from the filtrate using a rotary evaporator. The collected material is difficult to dry completely ($^1$H NMR shows a trace amount of ethyl acetate solvent). Thus, the collected material is dried in a rotary evaporator at 40° C. for 2 hours, and in a vacuum oven at 40° C. overnight, yielding 7.47 grams of a light yellowish oil, the 3-(2,5-dioxotetrahydrofuran-3-yl)-2-methylpropane-1-sulfonyl chloride, depicted as Structure (3b) in Equation (2b) above. The reaction achieves a 72.5% yield of 3-(2,5-dioxotetrahydrofuran-3-yl)-2-methylpropane-1-sulfonyl chloride.

$^1$H NMR (500 MHz, CDCl$_3$, 25° C., mixture of isomers in 1:1.1 ratio): δ 3.80-3.70 (m, 3H), 3.67 (dd, J=14.3, 6.5 Hz, 1H), 3.27-3.11 (m, 4H), 2.76-2.68 (m, 2H), 2.68-2.59 (m, 1H), 2.48-2.37 (m, 1H), 2.27-2.18 (m, 1H), 2.05-1.92 (m, 2H), 1.73-1.64 (m, 1H), 1.28 (d, J=6.8 Hz, 3H), 1.24 (d, J=6.8 Hz, 3H).

$^{13}$C NMR (126 MHz, CDCl$_3$, 25° C., mixture of isomers in 1:1.1 ratio): δ 173.40, 173.16, 169.51, 169.46, 71.39, 71.07, 38.28, 38.16, 37.03, 36.43, 34.80, 34.05, 28.84, 28.76, 19.61, 18.51.

HR GC/MS/EI (PCI—NH$_3$) (M+NH$_4$)$^+$: m/z calculated for C$_8$H$_{15}$ClNO$_5$S$^+$: 272.0359, found: 272.03550 and 272.03609.

FTIR (cm$^{-1}$): 1865 (C=O), 1778 (C=O).

3. Azidization of 3-(2,5-dioxotetrahydrofuran-3-yl)-2-methylpropane-1-sulfonyl chloride The azidization of 3-(2,5-dioxotetrahydrofuran-3-yl)-2-methylpropane-1-sulfonyl chloride is depicted in Equation (3b):

Equation (3b)

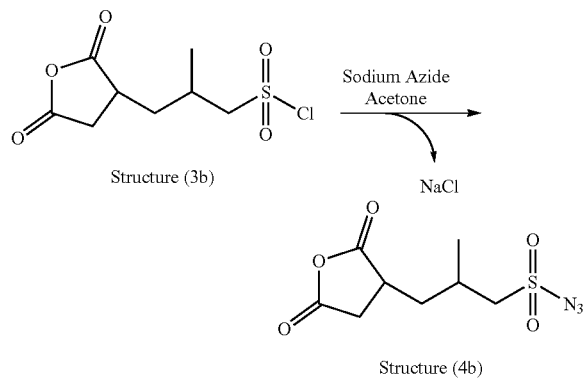

Sodium azide is measured inside a fume hood using a plastic spatula. The sodium azide is placed in a 250 mL round bottom flask and a glass stopper is placed on the flask. The weight of the sodium azide inside the flask is measured, using a balance outside the fume hood, to be 0.88 grams (0.0135 mol) sodium azide. Subsequently, acetone is included in the flask (the total amount of acetone used in the azidization step is 45 mL). In a separate 250 mL round bottom flask is placed 3.13 grams (0.0122 mol) of 3-(2,5-dioxotetrahydrofuran-3-yl)-2-methylpropane-1-sulfonyl chloride, which is dissolved in a minimum amount of acetone. Subsequently, the 3-(2,5-dioxotetrahydrofuran-3-yl)-2-methylpropane-1-sulfonyl chloride/acetone solution is transferred to the flask containing the sodium azide/acetone solution. After the transfer, the flask originally containing the 3-(2,5-dioxotetrahydrofuran-3-yl)-2-methylpropane-1-sulfonyl chloride/acetone solution is rinsed with a few milliliters of acetone to ensure all of the material is transferred to the round bottom flask originally containing the sodium azide/acetone solution.

A magnetic stir bar is included in the flask (containing the 3-(2,5-dioxotetrahydrofuran-3-yl)-2-methylpropane-1-sulfonyl chloride/acetone/sodium azide solution). The flask is connected to a condenser. The cooling system for the condenser is air. Subsequently, the solution is stirred overnight at room temperature (23° C.) under a $N_2$ atmosphere inside the fume hood. After a few hours, a white precipitate is observed in the flask. The next day, the solvent is completely evaporated using a rotary evaporator to produce a yellowish residue. Then, 50 mL ethyl acetate is included with the residue. The yellowish residue is soluble in ethyl acetate and the white precipitate is not. The mixture is washed twice with 30 mL water per wash, and 30 mL of ethyl acetate is included. An organic layer forms. The organic layer is separated, dried with magnesium sulfate, and filtered using a fritted glass funnel. The remaining solvent is removed from the filtrate using a rotary evaporator at 40° C. The material is then dried in a vacuum oven at 40° C. overnight to yield 2.5 grams of a yellow/brownish oily product, the 3-(2,5-dioxotetrahydrofuran-3-yl)-2-methylpropane-1-sulfonyl azide, depicted as Structure (4b) in Equation (3b) above. The reaction achieves a 77.8% yield of 3-(2,5-dioxotetrahydrofuran-3-yl)-2-methylpropane-1-sulfonyl azide.

$^1$H NMR (500 MHz, CDCl$_3$, 25° C., mixture of isomers in a 1:1.1 ratio): trace ethyl acetate in sample, δ 3.39-3.29 (m, 3H), 3.27 (ddd, J=14.6, 6.5, 0.5 Hz, 1H), 3.24-3.10 (m, 4H), 2.76-2.65 (m, 2H), 2.58-2.45 (m, 1H), 2.35-2.25 (m, 1H), 2.25-2.17 (m, 1H), 2.01-1.91 (m, 2H), 1.70-1.60 (m, 1H), 1.24 (d, J=6.8, 3H), 1.21 (d, J=6.8, 3H).

$^{13}$C NMR (126 MHz, CDCl$_3$, 25° C., mixture of isomers in a 1:1 ratio): δ 173.58, 173.34, 169.63, 169.58, 61.59, 61.34, 38.45, 38.36, 37.43, 36.82, 34.94, 34.21, 27.98, 27.89, 19.96, 18.85.

APCI/FIA/MS (M+NH$_4$)$^+$: calculated for C$_8$H$_{15}$N$_4$O$_5$S$^+$: 279.0763, found=279.07615.

APCI/FIA/MS/MS (M+H)$^+$: calculated for C$_8$H$_{12}$N$_3$O$_5$S$^+$: 262.0497, found=262.05.

FTIR (cm$^{-1}$): 2132 (N$_3$), 1857 (C=O), 1771 (C=O).

It is specifically intended that the present disclosure not be limited to the embodiments and illustrations contained herein, but include modified forms of those embodiments including portions of the embodiments and combinations of elements of different embodiments as come within the scope of the following claims.

We claim:

1. A process comprising:
   (i) thio-acetoxylating an alkenyl carboxylic acid anhydride to form a thioacetate anhydride intermediate;
   (ii) oxychlorinating the thioacetate anhydride intermediate to form a sulfonyl chloride anhydride intermediate; and
   (iii) azidizing the sulfonyl chloride anhydride intermediate to form an aliphatic sulfonyl azide anhydride having a Structure (4):

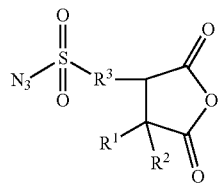

Structure 4 wherein R$^1$, R$^2$, and R$^3$ may be the same or different; and R$^1$, R$^2$, and R$^3$ each is independently selected from a substituted C$_1$-C$_{40}$ hydrocarbonyl group, an unsubstituted C$_1$-C$_{40}$ hydrocarbonyl group, Si(R$^C$)$_3$, OR$^C$, R$^C$C(O)O—, R$^C$OC(O)—, R$^C$C(O)N(R)—, (R$^C$)$_2$NC(O)—, a halogen atom, and a hydrogen atom, wherein R$^C$ is a C$_1$-C$_{30}$ hydrocarbonyl group;

with the proviso that at least one of R$^1$, R$^2$, and R$^3$ is selected from a substituted C$_1$-C$_{40}$ hydrocarbonyl group or an unsubstituted C$_1$-C$_{40}$ hydrocarbonyl group, and the aliphatic sulfonyl azide anhydride excludes an aromatic sulfonyl azide anhydride.

2. The process of claim 1 wherein the thio-acetoxylating comprises reacting the alkenyl carboxylic acid anhydride with a thioacetic acid in the presence of a radical initiator to form the thioacetate anhydride intermediate.

3. The process of claim 1 wherein the thio-acetoxylating comprises reacting the alkenyl carboxylic acid anhydride with a thioacetic acid in the presence of an azo-containing radical initiator at a temperature from 50° C. to 90° C. to form the thioacetate anhydride intermediate.

4. The process of claim 1 wherein the oxychlorinating comprises reacting the thioacetate anhydride intermediate with a chlorine source to form the sulfonyl chloride anhydride intermediate.

5. The process of claim 1 wherein the oxychlorinating comprises reacting the thioacetate anhydride intermediate with N-chlorosuccinimide in the presence of a hydrochloric acid aqueous solution at a temperature from 0.1° C. to 22° C. to form the sulfonyl chloride anhydride.

6. The process of claim 1 wherein the oxychlorinating comprises reacting the thioacetate anhydride intermediate with chlorine gas in the presence of water at a temperature from 0.1° C. to 22° C. to form the sulfonyl chloride anhydride intermediate.

7. The process of claim 1 wherein the azidizing comprises reacting the sulfonyl chloride anhydride intermediate with sodium azide in the presence of acetone to form the aliphatic sulfonyl azide anhydride.

8. The process of claim 1 wherein the azidizing comprises reacting the sulfonyl chloride anhydride intermediate with sodium azide in the presence of acetone at a temperature from 20° C. to 25° C. to form the aliphatic sulfonyl azide anhydride.

9. The process of claim 1 comprising:
(i) thio-acetoxylating endo-cis-bicyclo[2.2.1]hept-5-ene-2,3-dicarboxylic anhydride to form 5-(thioacetoxy)endo-cis-bicyclo[2.2.1]hept-5-ene-2,3-dicarboxylic anhydride;
(ii) oxychlorinating the 5-(thioacetoxy)endo-cis-bicyclo [2.2.1]hept-5-ene-2,3-dicarboxylic anhydride to form 5-(chlorosulfonyl)endo-cis-bicyclo[2.2.1]heptane-2,3-dicarboxylic anhydride; and
(iii) azidizing the 5-(chlorosulfonyl)endo-cis-bicyclo [2.2.1]heptane-2,3-dicarboxylic anhydride to form 5-(azidosulfonyl)endo-cis-bicyclo[2.2.1]heptane-2,3-dicarboxylic anhydride.

10. The process of claim 1 comprising:
(i) thio-acetoxylating 2-methyl-2-propen-1-yl succinic anhydride to form S-(3-(2,5-dioxotetrahydrofuran-3-yl)-2-methylpropyl) ethanethioate;
(ii) oxychlorinating the S-(3-(2,5-dioxotetrahydrofuran-3-yl)-2-methylpropyl) ethanethioate to form 3-(2,5-dioxotetrahydrofuran-3-yl)-2-methylpropane-1-sulfonyl chloride; and
(iii) azidizing the 3-(2,5-dioxotetrahydrofuran-3-yl)-2-methylpropane-1-sulfonyl chloride to form 3-(2,5-dioxotetrahydrofuran-3-yl)-2-methylpropane-1-sulfonyl azide.

11. A composition comprising an aliphatic sulfonyl azide anhydride having a Structure (4):

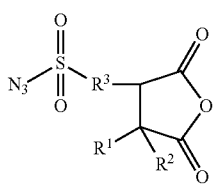

Structure (4)

wherein $R^1$, $R^2$, and $R^3$ may be the same or different; and $R^1$, $R^2$, and $R^3$ each is independently selected from a substituted $C_1$-$C_{40}$ hydrocarbonyl group, an unsubstituted $C_1$-$C_{40}$ hydrocarbonyl group, $Si(R^C)_3$, $OR^C$, $R^CC(O)O—$, $R^COC(O)—$, $R^CC(O)N(R)—$, $(R^C)_2NC(O)—$, a halogen atom, and a hydrogen atom, wherein $R^C$ is a $C_1$-$C_3$ hydrocarbonyl group;

with the proviso that at least one of $R^1$, $R^2$, and $R^3$ is selected from a substituted $C_1$-$C_{40}$ hydrocarbonyl group or an unsubstituted $C_1$-$C_{40}$ hydrocarbonyl group, and the aliphatic sulfonyl azide anhydride excludes an aromatic sulfonyl azide anhydride.

12. The composition of claim 11, wherein $R^2$ is hydrogen; and the $R^1$ and $R^3$ groups form an unsubstituted $C_3$-$C_8$ hydrocarbonyl group ring structure.

13. The composition of claim 11, wherein aliphatic sulfonyl azide anhydride is 5-(azidosulfonyl)endo-cis-bicyclo [2.2.1]heptane-2,3-dicarboxylic anhydride having a Structure (4a):

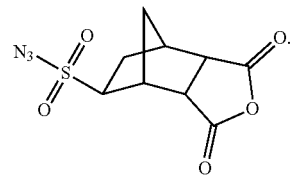

Structure (4a)

14. The composition of claim 11, wherein $R^1$ and $R^2$ each is hydrogen; and $R^3$ is an unsubstituted $C_1$-$C_{12}$ hydrocarbonyl group.

15. The composition of claim 14, wherein the aliphatic sulfonyl azide anhydride is 3-(2,5-dioxotetrahydrofuran-3-yl)-2-methylpropane-1-sulfonyl azide having a Structure (4b):

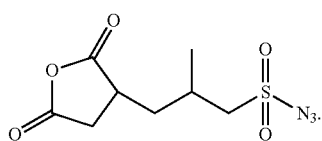

Structure (4b)

* * * * *